United States Patent [19]

Shirahata

[11] Patent Number: 5,068,386

[45] Date of Patent: Nov. 26, 1991

[54] PREPARATION OF TERTIARY-HYDROCARBYLSILYL COMPOUNDS

[75] Inventor: Akihiko Shirahata, Yotsukaido, Japan

[73] Assignee: Dow Corning Toray Silicone Company, Ltd., Tokyo, Japan

[21] Appl. No.: 531,617

[22] Filed: Jun. 1, 1990

[30] Foreign Application Priority Data

Jun. 28, 1989 [JP] Japan .................................. 1-165760

[51] Int. Cl.$^5$ .............................................. C07F 7/08
[52] U.S. Cl. .................................................. 556/480
[58] Field of Search ......................................... 556/480

[56] References Cited

U.S. PATENT DOCUMENTS

| | | | |
|---|---|---|---|
| 4,593,112 | 6/1986 | Takamizawa et al. | 556/480 |
| 4,650,891 | 3/1987 | Lennon | 556/480 |
| 4,672,135 | 6/1987 | Lennon | 556/480 |

OTHER PUBLICATIONS

Takamizawa; Tertiary Hydrocarbylsilyl-Compounds; Kokai No. 60-222492, Chem. Abs. 104:109950b.
Takamizawa; Tertiary Hydrocarbon Silyl Compounds; Kokai No. 60-237092, Chem. Abs. 104:149165f.

*Primary Examiner*—Paul F. Shaver
*Attorney, Agent, or Firm*—William F. Boley

[57] ABSTRACT

The present invention relates to a method for the preparation of tertiary-hydrocarbylsilyl compounds through a Grignard reaction. A Grignard reagent of formula RMgX, in which R is a tertiary-hydrocarbyl group and X is a halogen atom, is reacted with a silicon compound of formula $R^1_a SiX_{4-a}$; where $R^1$ is a substituted or unsubstituted monovalent hydrocarbon group and a is an integer with a value of zero to three. The process is ran in the presence of a catalytic quantity of a cyano compound or a thiocyanate compound.

12 Claims, No Drawings

PREPARATION OF TERTIARY-HYDROCARBYLSILYL COMPOUNDS

BACKGROUND OF INVENTION

The present invention relates to a method for the preparation of tertiary-hydrocarbylsilyl compounds, and, more particularly, relates to a method for the preparation of tert-hydrocarbylsilyl compounds through a Grignard reaction.

The following methods are known for the preparation of tert-hydrocarbylsilyl compounds:

(1) the reaction of tert-alkyllithium with chlorosilanes, and (2) in an improvement of the preceding method, the reaction of a tert-alkyl Grignard reagent with chlorosilanes (Japanese Patent Application Laid Open, Kokai, Number 60-222492, 222,492/85, and Japanese Patent Application Laid Open Number 60-237092, 237,092/85).

However, method (1) is associated with the following problems, which serve to make production on an industrial scale fairly difficult.

1. Generation of the starting tert-alkyllithium entails the preparation of a highly active lithium microdispersion at high temperatures (approximately 200 degrees Centigrade), which must then be reacted with a tert-alkyl halide using pentane solvent (low-boiling hydrocarbon) in an argon current. These circumstances demand careful attention with regard to reaction management, and the reaction must be run in a special vessel.

2. The obtained tert-alkyllithium is a very hazardous reagent which will autoignite merely upon contact with the atmosphere.

In the case of method (2), a tert-alkylchlorosilane is obtained by the reaction of a tert-alkyl Grignard reagent with SiH-containing (low sterically hindered) chlorosilanes such as trichlorosilane or methyldichlorosilane, or by the reaction of a tert-alkyl Grignard reagent with a disilane such as dimethyltetrachlorodisilane or hexachlorodisilane. Considering, for example, the use of this synthetic method to prepare the practically useful silylating agent, tert-butyldimethylchlorosilane, the reaction of methyldichlorosilane and a tert-butyl Grignard reagent presents itself. However, because the product here is tert-butylmethylchlorosilane, the residual chlorine group must be methylated by reaction with a methyl Grignard reagent and the SiH group must finally be chlorinated with chlorine in order to obtain the desired tert-butyldimethylchlorosilane. Moreover, in the case of the reaction of dimethylchlorosilane with a tert-butyl Grignard reagent, the SiH group must be chlorinated with chlorine in order to obtain the desired tert-butyldimethylchlorosilane (Japanese Patent Application Laid Open Number 60-222492). In the case of the reaction of hexachlorodisilane with a tert-butyl Grignard reagent, a partial methylation is necessary to obtain tert-butyldimethylchlorosilane (Japanese Patent Application Laid Open Number 60-237092). Thus, the former method suffers from a lengthy synthetic route, while the latter method requires special disilanes and, moreover, utilizes only half of the silicon.

Accordingly, the object of the present invention is a solution to the preceding defects encumbering the prior art based on the introduction of a simple, high-yield method for the preparation of tert-hydrocarbylsilyl compounds.

The method of the present invention provides for the simple, high-yield preparation of the desired tert-hydrocarbylsilyl compounds. As a particular matter, the preparative method of the present invention offers the advantage of the facile, high-yield preparation by a single-step reaction of tert-hydrocarbylsilyl compounds such as tert-butyldimethylchlorosilane which are extremely useful as silylating agents and are effectively used in the synthesis of steroids, prostaglandins, and so forth.

DESCRIPTION OF THE INVENTION

The present invention relates to a method for the preparation of tert-hydrocarbylsilyl compounds which is characterized by reacting a Grignard reagent with the following general formula $$R \, Mg \, X;$$

wherein R is a tert-hydrocarbyl group and X is a halogen atom; with a silicon compound with the following general formula $$R^1_a SiX_{4-a};$$

wherein $R^1$ is a substituted or unsubstituted monovalent hydrocarbon group, X is a halogen atom, and a is an integer with a value of zero to three; in the presence of a cyano compound or a thiocyanate compound.

Thus, as the result of various investigations directed at an industrial method for the preparation of tert-hydrocarbylsilyl compounds, the present inventor discovered that an addition reaction between a Grignard reagent as represented by the general formula $$R \, Mg \, X;$$

wherein R is a tert-hydrocarbyl group and X is a halogen atom; and a silicon compound as represented by the general formula $$R^1_a SiX_{4-a};$$

wherein $R^1$ is a substituted or unsubstituted monovalent hydrocarbon group, X is a halogen atom, and a is an integer with a value of zero to three; for which it was heretofore held that no reaction occurs, occurs in the presence of a cyano compound or a thiocyanate compound to afford the tert-hydrocarbylsilyl compound. The present invention was achieved based on this finding.

The Grignard reagent to be used by the preparative method of the present invention has the following general formula $$R \, Mg \, X.$$

The group R in this formula comprises tert-hydrocarbyl groups as exemplified by tert-alkyl groups such as tert-butyl, 1,1-dimethylpropyl, and 1,1-diethylpropyl, and by aryl group-containing tert-alkyl groups such as 1,1-dimethylbenzyl. X is a halogen atom as illustrated by the chlorine atom, bromine atom, and iodine atom. The Grignard reagent under consideration is thus exemplified by t-butylmagnesium chloride, 1,1-dimethylpropylmagnesium chloride, 1,1-diethylpropylmagnesium chloride, and 1,1-dimethylbenzylmagnesium chloride.

Considering the silicon compound with general formula $R^1_a SiX_{4-a}$ for reaction with the above tert-hydrocarbyl Grignard reagent, the former's group $R^1$ is exemplified by alkyl groups such as methyl, ethyl, and propyl; by alkenyl groups such as vinyl and allyl; by aryl groups such as phenyl and naphthyl; and by the benzyl group. X is a halogen atom such as the chlorine, bromine, or iodine atom. Thus, examples here are dimethyldichlorosilane, methyltrichlorosilane, tetrachlorosilane, phenyltrichlorosilane, diphenyldichlorosilane, vinyltrichlorosilane, methylvinyldichlorosilane, and allyltrichlorosilane. From the standpoint of reactivity, values of 1 and 2 are preferred for a in the general formula $R^1_a SiX_{4-a}$.

The cyano compound and thiocyanate compound encompass the metal salts and ammonium salts of hydrocyanic acid and thiocyanic acid as well as their silyl and tin compounds. Concrete examples in this regard are silver cyanide, copper cyanide, mercury cyanide, trimethylsilyl cyanide, tributyltin cyanide, copper thiocyanate, silver thiocyanate, calcium thiocyanate, sodium thiocyanate, and tetrabutylammonium thiocyanate. The cyano compound or thiocyanate compound may be used in this reaction in catalytic quantities. In this case, a catalytic quantity denotes quantities on the level of 0.01 mole % to 10 mole % and preferably in the range of 0.1 mole % to 2 mole %, in each case based on the reagents. Very small quantities of catalyst are disadvantageous from the standpoint of the reaction rate. On the other hand, almost no change in effect is associated with the use of very large quantities, and merely increasing the quantity of catalyst becomes economically disadvantageous.

The use of an organic solvent in the reaction under consideration is preferred in terms of controlling the reaction rate and stirring efficiency. The organic solvents typically used in Grignard reagent reactions may be used here, but ether solvents such as diethyl ether, tetrahydrofuran, and so forth are particularly preferred as this organic solvent. However, within the context of controlling the reaction, another inert solvent may also be present, for example, a hydrocarbon solvent such as benzene, toluene, and so forth.

The reaction should be conducted in the temperature range of $-20$ to 150 degrees Centigrade and preferably within the temperature range of zero to 100 degrees Centigrade.

Considering the structure of the target tert-hydrocarbylsilyl compound, the tert-hydrocarbyl group originating with the starting Grignard reagent will be present in the final compound directly bonded to the silicon atom, while the 3 remaining substituents on the silicon atom are exemplified by halogen atoms and/or substituted or unsubstituted monovalent hydrocarbon groups (such as alkyl groups, alkenyl groups, aryl groups, and the benzyl group) originating with the starting silicon compound. Furthermore, each molecule may contain more than one tert-hydrocarbyl group. The compounds under consideration are concretely exemplified by tert-butyldimethylchlorosilane, tert-butyldiphenylchlorosilane, tert-butylmethyldichlorosilane, tert-butylmethylphenylchlorosilane, tert-butylvinyldichlorosilane, tert-butyltrichlorosilane, 1,1-dimethylbenzyldimethylchlorosilane, 1,1-dimethylbenzylmethyldichlorosilane, 1,1-dimethylpropyldimethylchlorosilane, 1,1-dimethylpropylmethyldichlorosilane, and 1,1-dimethylpropyltrichlorosilane.

The present invention is concretely explained below with reference to illustrative examples. The products in the examples were confirmed from their NMR, IR, GC-MS, etc., spectra.

EXAMPLE 1

12.2 g (0.5 mol) magnesium was introduced into a 500 mL four-neck flask equipped with a reflux condenser, addition funnel, thermometer, and stirring rod. After drying under a nitrogen atmosphere, the tert-butyl Grignard reagent was prepared by the addition of 250 mL tetrahydrofuran and 46.3 g (0.5 mol) tbutyl chloride with stirring. To this was added 0.45 g (0.005 mol) copper cyanide at room temperature, and 64.5 g (0.5 mol) dimethyldichlorosilane was then dripped in while stirring. The temperature in the system rose to 60 degrees Centigrade. After heating with stirring under reflux for 3 hours, the addition of 100 mL hexane, filtration, distillation of the solvent from the filtrate, and continuing with distillation at ambient pressure gave 60 g (yield=80%) tert-butyldimethylchlorosilane.

EXAMPLE 2

12.2 g (0.5 mol) magnesium was introduced into a 500 mL four-neck flask equipped with a reflux condenser, addition funnel, thermometer, and stirring rod. After drying under a nitrogen atmosphere, the tert-butyl Grignard reagent was prepared by the addition of 250 mL tetrahydrofuran and 46.3 g (0.5 mol) t-butyl chloride with stirring. To this was added 0.45 g (0.005 mol) copper cyanide at room temperature, and 126.6 g (0.5 mol) diphenyldichlorosilane was then dripped in while stirring. The system temperature rose to 50 degrees Centigrade. After heating and stirring under reflux for 5 hours, the addition of 100 mL hexane, filtration, distillation of the solvent, and continuing with distillation in vacuo gave 103 g (yield =75%) tert-butyldiphenylchlorosilane.

EXAMPLE 3

12.2 g (0.5 mol) magnesium was introduced into a 500 mL four-neck flask equipped with a reflux condenser, addition funnel, thermometer, and stirring rod. After drying under a nitrogen atmosphere, the tert-butyl Grignard reagent was prepared by the addition of 250 mL tetrahydrofuran and 46.3 g (0.5 mol) t-butyl chloride with stirring. To this was added 0.34 g (0.004 mol) sodium thiocyanate at room temperature, and 64.5 g (0.5 mol) dimethyldichlorosilane was then dripped in while stirring. The system temperature rose to 60 degrees Centigrade. After heating and stirring under reflux for 3 hours, the addition of 100 mL hexane, filtration, distillation of the solvent from the filtrate, and continuing with distillation at ambient pressure gave 59 g (yield=78%) tert-butyldimethylchlorosilane.

EXAMPLE 4

12.2 g (0.5 mol) magnesium was placed in a 500 mL four-neck flask equipped with a reflux condenser, addition funnel, thermometer, and stirring rod. After drying under a nitrogen atmosphere, the tert-butyl Grignard reagent was prepared by the addition of 250 mL tetrahydrofuran and 46.3 g (0.5 mol) t-butyl chloride with stirring. To this was added 0.34 g (0.004 mol) sodium thiocyanate at room temperature, and 74.9 g (0.5 mol) methyltrichlorosilane was then dripped in with stirring and ice cooling. The system temperature was maintained below 10 degrees Centigrade. After the completion of addition, the temperature was returned to room temperature and the reaction was stirred for 3 hours. The addition of 100 mL hexane, filtration, distillation of the solvent from the filtrate, and continuing with distillation at ambient pressure gave 64 g (yield=75%) tert-butylmethyldichlorosilane.

What is claimed is:

1. A method for preparation of tertiary-hydrocarbylsilyl compounds comprising reacting a Grignard reagent of formula $$R\,Mg\,X;$$

wherein R is a tertiary-hydrocarbyl group and X is a halogen atom;

with a silicon compound of formula $$R^1{}_a SiX_{4-a};$$

wherein $R^1$ is a substituted or unsubstituted monovalent hydrocarbon group, X is a halogen atom, and a is an integer with a value of zero to three;

in the presence of a cyano compound or thiocyanate compound.

2. A method according to claim 1, where R is a tertiaryalkyl group and X is a chlorine atom.

3. A method according to claim 1, where R is a radical selected from a group consisting of tert-butyl, 1,1-dimethylpropyl, 1,1-diethylpropyl, and 1,1-dimethylbenzyl and X is a chlorine atom.

4. A method according to claim 1, where a is 1 or 2 and $R^1$ is a radical selected from a group consisting of methyl, ethyl, propyl, vinyl, and allyl.

5. A method according to claim 1, where a is 1 or 2 and $R^1$ is a radical selected from a group consisting of methyl, ethyl, propyl, vinyl, allyl, phenyl, naphthyl, and benzyl.

6. A method according to claim 1, where the cyano compound is selected from a group consisting of silver cyanide, copper cyanide, mercury cyanide, trimethylsilyl cyanide, and tributyltin cyanide.

7. A method according to claim 1, where the thiocyanate compound is selected from a group consisting of copper thiocyanate, silver thiocyanate, calcium thiocyanate, sodium thiocyanate, and tetrabutylammonium thiocyanate.

8. A method according to claim 1, where the cyano compound or thiocyanate compound is present at a level of 0.01 to 10 mole percent.

9. A method according to claim 1, where the cyano compound or thiocyanate compound is present at a level of 0.1 to 2 mole percent.

10. A method according to claim 1, further comprising the presence of an organic solvent.

11. A method according to claim 10, where the organic solvent is an ether.

12. A method according to claim 1, where reacting the Grignard reagent with the silicon compound is conducted within a temperature range of zero to 100° C.

* * * * *